(12) United States Patent
Menjoge et al.

(10) Patent No.: US 7,378,109 B2
(45) Date of Patent: May 27, 2008

(54) PHARMACEUTICAL COMPOSITION FOR IMPROVING PALATABILITY OF DRUGS AND PROCESS FOR PREPARATION THEREOF

(75) Inventors: Anupa R. Menjoge, Maharashtra (IN); Mohan G. Kulkarni, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 395 days.

(21) Appl. No.: 11/019,648

(22) Filed: Dec. 23, 2004

(65) Prior Publication Data

US 2006/0141053 A1 Jun. 29, 2006

(51) Int. Cl.
*A61K 9/14* (2006.01)

(52) U.S. Cl. ..................... 424/487; 424/483

(58) Field of Classification Search ................ 424/472, 424/483, 487
See application file for complete search history.

(56) References Cited

U.S. PATENT DOCUMENTS

| | | | |
|---|---|---|---|
| 4,786,508 A | * | 11/1988 | Ghebre-Sellassie et al. 424/482 |
| 4,865,851 A | * | 9/1989 | James et al. ................ 424/498 |
| 6,197,348 B1 | * | 3/2001 | Morella et al. ............. 424/497 |
| 2002/0119195 A1 | | 8/2002 | Sen et al. |
| 2003/0064108 A1 | * | 4/2003 | Lukas et al. ................ 424/495 |
| 2005/0136114 A1 | | 6/2005 | Kulkarni et al. |
| 2005/0136115 A1 | | 6/2005 | Kulkarni et al. |
| 2005/0137372 A1 | | 6/2005 | Kulkarni et al. |
| 2005/0281874 A1 | | 12/2005 | Menjoge et al. |
| 2006/0134054 A1 | | 6/2006 | Kulkarni et al. |
| 2006/0141053 A1 | | 6/2006 | Menjoge et al. |
| 2007/0072996 A1 | | 3/2007 | Kedar et al. |
| 2007/0073014 A1 | | 3/2007 | Kedar et al. |
| 2007/0122375 A1 | | 5/2007 | Gore et al. |

* cited by examiner

*Primary Examiner*—Sharon E. Kennedy
(74) *Attorney, Agent, or Firm*—Nixon & Vanderhye P.C.

(57) ABSTRACT

The present invention discloses compositions, comprising a lipid-polymer matrix to mask the bitter or unpleasant taste of the medicament. The lipid or a blend of lipids, are used in combination with the pH dependent polymer where the said polymer is acid soluble or swellable The process for the preparation of taste masked pharmaceutical compositions of the bitter drugs comprising the said lipid-polymer compositions are disclosed. The concomitant use of the acid soluble polymer, which remains collapsed at the pH of saliva, inhibits the release of drug at that pH and hence they further help in bitterness inhibition. The said compositions deliver substantial amount of the bitter drug immediately at the gastric pH with improved palatability.

51 Claims, No Drawings

PHARMACEUTICAL COMPOSITION FOR IMPROVING PALATABILITY OF DRUGS AND PROCESS FOR PREPARATION THEREOF

FIELD OF INVENTION

The present invention provides a pharmaceutical composition for improving palatability of drugs. More particularly the present invention relates to bitterness inhibition of drugs by dispersing the drug in a lipid-polymer matrix. The pharmaceutical compositions of the present invention release substantial amount of the drug immediately at the gastric pH. The present invention also relates to the process for the preparation of these compositions

BACKGROUND OF INVENTION

Although a variety of delivery systems are being developed for different routes of administration like the oral, parenteral, nasal and transdermal, the oral route remains attractive for drug delivery because this mode of administration is an easy, convenient, noninvasive and familiar method of drug delivery. The common oral dosage forms include: liquid mixtures like solutions, suspensions, solid dosage forms like tablets and capsules and liquid filled capsules etc. The solid dosage forms are further modified depending on the therapeutic action desired, like controlled, extended or delayed release. However, patients at the extremes of age, such as children and the elderly, often experience difficulty in swallowing solid oral dosages forms. For these patients the drugs are mostly provided in liquid dosage forms such as solutions, emulsions and suspensions. These dosage forms usually lead to perceptible exposure of the active drug ingredient to taste buds and this is a very serious problem when the drug has an extremely unpleasant or bitter taste.

The bitter taste of the drugs, which are orally administered, is disadvantageous in several aspects Taste is an important parameter governing the compliance. The disagreeable taste of drugs causes difficulties in swallowing or causes patients to avoid their medication thereby resulting in low compliance of patients. Conventional taste masking techniques such as use of sweeteners, amino acids, flavoring agents are often unsuccessful in masking the taste of the highly bitter drugs like quinine, barberin, etoncoxib, antibiotics like levofloxacin, ofloxacin, sparfloxacin, ciprofloxacin, celbroxime axetil, erythromycin and clarithromycin. Thus taste-masking technologies are considered important and developed by many researchers Taste masking is a major problem when the drugs are extremely unpleasant and bitter and this problem is not restricted to the liquid oral compositions like solutions, dry syrups and suspensions but may also be encountered during the formulation of chewable tablets or dispersible tablets wherein these dosage forms usually lead to perceptible exposure of active ingredient to taste buds Depending on the type of dosage form, various methods have been employed to overcome the unpleasant taste and bitterness of the drug. Various methods for taste masking have been tried earlier, which include use of ion exchange resins, complexation of bitter drugs with pharmaceutically acceptable excipients and coating of drugs by lipids and various polymeric materials. Some of the highly bitter drugs are formulated using lipids.

U.S. Pat. No. 4,797,288 discloses a novel drug delivery system based on the hydrophobic matrix coating the core, such that the coating delays the hydration of the core. The delivery system comprises of dry drug particles designed either for chewing or swallowing. The hydrophobic matrix coating delaying the hydration of core comprised of about 200-400% by weight of the drug. The hydrophobic material had a melting point in the range of 25-100° C. The delivery system comprised of 61-95% by weight of fatty acid GB Patent 1323161 discloses coating of acetoxymethyl benzylpenicillinate using lipids having a melting point of not more than 95° C. The coating of the lipid is achieved by spray congealing method. The coated powder is reconstituted at a pH of 6.5. The composition protects penicillin from moisture and also masks the bitter taste. However the use of lipids alone tends to delay the release of the drug owing to the hydrophobic nature of the lipids.

GB Patent 2081092 discloses use of waxy materials and high molecular weight water swellable materials. The water swellable material is added to improve dissolution, which helps in increasing the absorption of the drug. However the use of water swelling materials alone with lipids in compositions is of limited use since these compositions would tend to leach the drugs in the aqueous media used for reconstitution of dry syrups or also in suspensions.

U.S. Pat. No. 5,405,617 discloses a solve-it-less method for preparation of the taste-masked composition involving spray congealing of molten stearyl stearate and admixing an active pharmaceutical therewith.

U.S. Pat. No. 4,865,851 discloses a method for taste masking highly bitter 1 acetoxy ethyl ester of cefuroxime in particulate form, by coating with an integral coating of lipid or a mixture of lipids to mask the taste. Coated particles are incorporated in aqueous suspensions The lipids used are insoluble in water but are dispersed or dissolved in gastrointestinal fluid The lipids used in the composition for taste masking are in the range of 95-10% and cefuroxime axetil is in the range of 5-90%. The preferred range of lipid is 90-70% and cefuroxime axetil is 10-30% The examples disclosed in the patent show a drug to lipid ratio of 1:4 and above Robson et al. (H J. Robson, D Q. M Craig, D. Deutsch, International Journal to Pharmaceutics, 190, 1999, 183-192) have studied the dissolution of stearic acid coated cefuroxime axetil microspheres in distilled water and Sorensen modified butter pH 5.9, 7 and pH 8. The study indicated that the release of the drug from stearic acid coated cefuroxime axetil microspheres would increase on reaching the intestine. The coating helped in taste masking of cefuroxime axetil. Robson et al. (H. J. Robson, D. Q. M. Craig, D. Deutsch, International Journal of Pharmaceutics 195, 2000, 137-145) have also disclosed the influence of buffer composition on the release of the cefuroxime axetil from stearic acid coated cefuroxime axetil microspheres The buffers studied included the Sorensen modified phosphate buffer, Citrate phosphate buffer, boric acid buffer and the phosphate buffer mixed, all with the pH range of 7 according to the pharmaceutical codex 1994. The study shows effect of the pH and concentration of the sodium ions on release mechanism. The interaction of the stearic acid with buffer media containing sodium ions is effective for the release mechanism.

In the above disclosures release of cefuroxime axetil was studied in basic media. Dantzig et al (Anne H. Dantzig, Dale C Duckworth, Linda B. Tabas, Biochimica et Biophysica Acta 1191, 1994, 7-13) show that cefuroxime axetil is hydrolyzed to cefuroxime in the intestinal lumen by the esterases reducing the cefuroxime axetil concentration in the lumen, and resulting in reduced absorption, leading to low bioavailability of Cefuroxime axetil in humans. Hence formulations of drugs like cefuroxime axetil should be such that they release the drug in the upper gastric region rather than at the intestinal pH. Cefuroxime axetil already has a low bioavailability of 32-50% and hence further reduction in the bioavailability due to the formulation aspects should be minimized.

U.S. Pat. No. 4,897,270 discloses film-coated tablets of cefuroxime axetil to taste mask the bitter drug such that the film coat ruptures in few seconds and tablet disintegrates immediately. This preparation is useful for improving bioavailability of cefuroxime axetil. It is taught that cefuroxime axetil, once in contact with aqueous medium, forms a gelatinous mass The gelling effect is temperature dependent and occurs at temperatures of −37° C., i.e. at the physiological temperature at which disintegration of orally administered tablets, takes place Further, it is further taught that a tablet having conventional film coat containing cefuroxime axetil in the core, when orally administered results in gelation of drug due to slow permeation of moisture across the film coat. Gel formation leads to poor disintegration of tablet core and hence to poor dissolution, absorption and bioavailability of cefuroxime axetil. Drugs like cefuroxime axetil should therefore be so formulated that the compositions release the drug immediately in the gastric region without slow permeation of the buffer in coating material. It is further taught that coating material for cefuroxime axetil should be such that it releases the drug immediately before gelling occurs U.S. Pat. No. 5,972,373 discloses the taste masking pharmaceutical compositions, which offer good bioavailability. The composition has a high polymer consisting of polyvinylacetal diethylaminoacetate, aminoalkylmethacrylate copolymer Eudragit E soluble in the stomach and a monoglyceride glyceryl monostearate used for taste masking. Such coating compositions would be of use for drugs such as cefuroxime axetil, which are better absorbed from the upper gastric region. However, cefuroxime axetil shows negative interaction with a polymer based on aminoalkylmethacrylate copolymer like Eudragit E.

Alonso et al (M. J Alonso, M. L. Lorenzo-Lamosa, M. Cuna, J. L. Vila-Jato and D. Torres, Journal of Microencapsulation, 1997, Volume 14, No 5, 607-616) studied encapsulation of cefuroxime axetil, a highly bitter drug, in pH sensitive acrylic microspheres in order to formulate a suspension dosage from. The study shows that cationic polymer Eudragit E (polymer containing dimethyl amino ethyl methacrylate) showed negative interaction with cefuroxime axetil.

U.S. Pat. No. 4,132,753 discloses a process for controlled release of medicament from a composition comprising wax like materials and having a melting point between 30-100° C. The lipid medicament mixture is agitated continuously at a temperature at which tie wax like material melts and the medicament powder sinks into the molten surfaces of the waxy material Coated granules were obtained by cooling molten mass followed by sizing. Wax like materials disclosed include glyceryl monostearate, hydrogenated fat and waxy aliphatic alcohol. U.S. Pat. No. 6,589,955 discloses a taste masked pediatric formulation of gatifloxacin. The taste masked co-precipitate of garifloxacin is formed with fatty acids like stearic acid or palmitic acid, the ratio of gatifloxacin to fatty acid being in a range of 1:1.8 to 1:2.3. The preferred ratio is 1:2.1. U.S. Pat. No. 6,156,339, discloses a process for preparation of a taste masked, solid oral rapidly disintegrating dosage form comprising water dispersible carrier, filler, pharmaceutical active and a lipid such that the pharmaceutical active is in association with the lipid Weight ratio of pharmaceutically active substance to lipid is in the range of 1:1 to 1:10.

Japanese Patent Application 2002138034 discloses a chewable tablet containing a bitter anitihistaminic drug, Chlorpheniramine maleate and fatty aced viz; stearic acid to mask the taste The composition contains fatty acid in the range of 0.5 pts wt to less than 3 pts. wt. of fatty acid per 1 pt. wt of the drug.

A chewable tablet with a medicament coated by lipid material is disclosed in French Patent 2784895 Lipid materials melting in a range of 37-75° C. are used The patent discloses 10%, preferably 2-5% or lipid being used for coating of the drug.

The lipid materials used in formulations like the crunchable/chewable tablets or granules for taste masking applications lead to the rapid release of the drug on fracturing of the lipid coat during the mastication, however this would lead to the perception of bitter taste.

U.S. Pat. No. 6,485,742 discloses coating of hydrophilic core material comprising vitamins, by drop wise addition of the molten lipid on a fluidized core material such that the molten lipid solidifies and forms a coat on the core material. Coating by lipid material masks the unpleasant flavor of the vitamin. The coating material is used in the range of 0.1 to 30% w/w of the total coated material. PCT International Application WO 00/61119 discloses a process for microencapsulation of a medicament by mixing the medicament with a coating agent, which is melted and kept under stirring. The melted material is cooled under stirring to yield the microcapsules.

U.S. Pat. No. 4,837,381 discloses a slow release microsphere preparation of a wax or fat containing the biologically active protein or peptide The invention discloses the use of 30-95% w/w of the fat or wax and 2-70% of the protein or peptide in the microsphere preparation.

Microspheres prepared by thermoforming of compositions containing pharmaceutical active in a range of 5-90%, 10-90% of glyceryl monostearate, and 2-15% of polyethylene glycol and glyceryl palmitostearate, are disclosed in the U.S. Pat. No. 6,117,452.

Japanese Patent Application 2001288117 discloses taste masking of oral preparation of drug rebamipide with fatty acid glycerol esters optionally with easily water-soluble substances. Water soluble or swelling substances are used to enhance release of the drug from lipid matrix. The use of water-soluble substances along with lipids limits their use in liquid oral preparation.

Pharmaceutical compositions with improved taste are disclosed in PCT International Application WO 00/06122. The drug is dispersed in fatty acid ester of glycerol base, 1.5 to 15 parts by weight based on 1 part of the drug. The fatty acid coated drug particles are further coated by water-soluble, water-insoluble or gastric soluble or an enteric polymer.

A substantially tasteless pharmaceutical delivery system is disclosed in EP 0670716. The delivery system comprises an active ingredient, a matrix of wax core material having a melting point in the range 50-200° C. and a hydrophobic polymer The amount of hydrophobic material present in the delivery system is 3-10% by weight of the matrix and the amount of the wax core present in the matrix is 15-85% by weight of the matrix.

Grains for oral administration obtained by spray solidification, which provide excellent taste-masking or bitter drugs, are disclosed in PCT International Application WO 00/18372 The grains contain a drug with unpleasant taste and a lipid carrier having melting point of 40 to 120° C. along with a polymer used to mask the unpleasant taste. The polymer used in combination with the lipid is either an enteric polymer or a gastric polymer.

PCT International Application WO 03/059349 discloses oral fast dispersing dosage form comprising microparticles for enhancing the bioavailability. The microparticles contain the drug zolpidem, fatty acids as spheronization aids like monoglycerides solubility enhancer like macrogol and the polymer coat to taste mask the product.

U.S. Patent Application Ser. No. 2004091536, discloses granules for dry reconstitutable telithromycin suspension comprising of the core of telithromycin and waxy material coated in succession by lipid and polymer coating twice and another coat containing optionally a lipid with the polymer Matrices containing the bitter drug clarithromycin, glycerol fatty acid ester or stearyl alcohol and polymer selected from hydroxypropyl methylcellulose phthalate, hydroxypropyl methylcellulose acetate succinate, carboxymethyl ethyl cellulose, methacrylic acid copolymer L, methacrylic acid copolymer LD and methacrylic acid copolymer S are disclosed in PCT International Application WO 01/91761. The matrices provide oral formulations free of the bitter taste of clarithromycin.

The following patents and patent applications disclose the use of lipids alone or lipids with other inactives like polymers in pharmaceutical compositions of the drugs: WO 02/72072; U.S. Pat. No. 4,880,634, U.S. Pat. No. 5,571,533; U.S. Pat. No. 5,169,645, U.S. Pat. No. 6,086,920, WO 99/32092; U.S. Pat. No. 5,891,476, EP 0855183.

Lipids are associated with properties like water repellency, non-toxicity and freedom from objectionable odor and color and they impart a smooth texture to the compositions. These properties make the lipids are good candidates for the taste masking applications. However fatty acids do exhibit good film forming hence integral coatings with lipids alone need larger amount of lipids since the medicament has to be dispersed completely in the lipid matrix. The techniques like the melt granulation and spray congealing also need large amount of the molten lipids since the drug is required to be dispersed within the lipid matrix.

Lipids are hydrophobic in nature and so the release of the medicament is greatly impaired when lipids are used in higher amounts. Many formulations disclosed above employ polymers in combination with the lipids to accelerate the release of the drug. The use of water swelling or soluble polymers along with lipids provide immediate release of the drugs as desired but cannot provide the desired taste masking effect, especially in case of the liquid oral compositions or granules for reconstitution. The use of pH independent polymers like ethyl cellulose in combination with lipids for taste masking provides compositions which prevent the leaching of the drug in the surrounding aqueous media as in case of liquid orals but the drug release is delayed on ingestion. Similarly the compositions employing enteric polymers in combination with lipids tend to delay the drug release till they reach the intestine.

Some of the patent applications disclosed above, use gastric soluble polymer Eudragit E in combination with the lipids, which provide an immediate release of the drug and also the taste masking effect However Eudragit E shows a swelling up to pH 5.5 exhibits an interaction with certain drugs like Cefuroxime axetil.

Hence there is a need to develop formulation such that the amount of the total polymer required for the taste masking application is reduced and yet the composition delivers substantial amount of the drug in the gastric region without delay. Further the polymer should be such that it provides for a wider range of pH, for reconstitution of taste masked granules.

We have now discovered that the pH sensitive polymer disclosed and claimed in our co-pending applications PCT/IN03/00390 and PCT/IN03/00392, when used in combination with lipids, such as fatty acids, fatty acid esters and fatty alcohols for coating of drugs show taste masking of bitter drugs at the pH of saliva. The amounts of polymer required to achieve effective taste masking are lower than in our co-pending patent applications PCT/IN03/00390, PCT/IN03/00392 and U.S. patent application Ser. No. 10/871,534. The amounts of lipids required to achieve taste masking are also significantly lower than those in U.S. Pat. No. 4,865,851 Further, the rates of release of drugs from lipid-polymer mixtures in this present invention are significantly higher than those, which can be attained from formulations based on lipids or mixtures of lipids, under identical conditions.

OBJECTS OF THE INVENTION

One object of the invention is to use a blend of pH dependent polymers with lipids, either alone or a blend of lipids.

Another object of the invention is to provide a taste masking formulation comprising a blend of a lipid(s) in combination with an acid soluble or swellable polymer, which enables delivery of substantial amount of drug immediately, while ensuring improved palatability Another object of the invention is to provide a pharmaceutical formulation wherein the drug is dissolved in the stomach essentially by using a specially synthesized pH sensitive polymer, which solubilizes or swells at acidic pH of the stomach but is insoluble at near neutral or neutral pH Another object of the invention is to provide a lipid-polymer matrix to coat a drug so that the amount of polymer required is lowered since it is used in combination with lipids, and the amount of lipid is also lowered due to the lipid-polymer matrix synergy which inhibits the bitter taste of the drug.

Another object of the invention is to use a lipid-polymer solution to coat a drug in order to lower the amount of lipid required, in comparison to the amount required for dispersion of drug in molten lipid for spray congealing or melt granulation.

Another object of the invention is to develop compositions, which can be used for taste masking of bitter drugs in various dosage forms, while enabling rapid release of the drug on ingestion and thus not altering the availability of the drugs.

It is a further object of the invention to provide a composition for taste masking of a drug, which does not release the drug at the pH of the saliva.

Yet another object of the invention is to develop taste masked particles which can be used in liquid orals like suspensions, dry syrups, and solid dosage form like chewable tablets, fast dispersible tablets and conventional tablets.

SUMMARY OF THE INVENTION

Accordingly, the present invention provides a pharmaceutical composition comprising a drug, a lipid component and a pH dependent polymer wherein the pH dependent polymer is acid soluble or swellable and has a formula: P [$A_{(x)}B_{(y)}C_{(z)}$] wherein P is polymer comprising (A) a hydrophobic monomer, (B) a basic monomer and (C) a hydrophilic monomer and (x)=30-95%, (y)=5-70%, (z)=0-60%, all expressed in terms of w/w such that, x+y+z=100%.

In one embodiment of the invention, the pH dependent polymer is selected from the group consisting of an acid soluble polymer or an acid swellable polymer, comprising of monomer methyl methacrylate, hydroxy ethyl methacrylate and vinyl pyridine in the range of 50-75%, 15-35% and about 5-15% w/w respectively.

In another embodiment of the invention, the lipid component is selected from fatty acids, esters of fatty acid, fatty alcohols, hydrocarbons, neutral fats and waxes.

In another embodiment of the invention, the fatty acid is selected from the group of saturated or unsaturated fatty acid.

In another embodiment of the invention, the saturated fatty acid comprises long chain aliphatic carboxylic acids such as lauric acid, stearic acid and palmitic acid.

In another embodiment of the invention, the fatty alcohol comprises long chain aliphatic alcohols such as stearyl alcohol, palmityl alcohol and cetyl alcohol.

In another embodiment of the invention, the esters of fatty acids comprises esters of glycerol with fatty acids such as glyceryl monostearate, glyceryl monopalmitate, glyceryl tripalmitate, glyceryl behenate and hydrogenated castor oil.

In another embodiment of the invention, the lipid component is used as a single lipid or a blend of lipids.

In another embodiment of the invention, the composition has a ratio of pH dependent polymer to lipid in the range of 1:0.5 to 1:40, preferably 1:1 to 1:35.

In another embodiment of the invention, the composition has a ratio of drug to lipid in the range of 1:0.1 to 1:8, preferably 1:0.4 to 1:6.

In another embodiment of the invention, the composition has a ratio of drug to pH dependent polymer in the range of 1:0.1 to 1:1, preferably 1:0.1 to 1:06.

In another embodiment of the invention, the drug is used as such or in the form of a pharmaceutically acceptable salt or ester or amide thereof.

In another embodiment of the invention, the drug is selected from the group of macrolide antibiotics like erythromycin, azithromycin and clarithromycin, fluroquinolones like ciprofloxacin, enrofloxacin, ofloxacin, gatifloxacin, levofloxacin and norfloxacin, cephalosporins consisting of cefuroxime, cefaclor, cephalexin, cephadroxil, cepfodoxime proxetil nonsteoroidal, and anti-inflammatory and analgesic drugs like of ibuprofen, aspirin, acetaminophen and diclofenac sodium; and COX 2 inhibitors like etoricoxib and celecoxib; antihistamic drugs like cimetidine, ranitidine, famotidine chlorpheniramine maleate, oxazolidinones like linezolid and other drugs like dextromethorphan.

In another embodiment of the invention, the composition does not release drug at pH of saliva but rapidly releases substantial amount of the drug at pH $\leq 3$ as found in the stomach.

In another embodiment of the invention, the composition is in the form of particles, with the drug dispersed within a polymer lipid matrix as such or is in a pharmaceutically acceptable dosage form In another embodiment of the invention, the pharmaceutical composition is in the form of a liquid oral such as dry syrup or suspension.

In another embodiment of the invention, the pharmaceutical composition is in the form of a solid dosage form like chewable, effervescent, rapidly disintegrating or dispersible tablets.

The present invention also provides a process for the preparation of a pharmaceutical composition comprising a drug, a lipid component and a pH dependent polymer wherein the pH dependent polymer is acid soluble or swellable and has a formula: P $[A_{(x)}B_{(y)}C_{(z)}]$ wherein P is polymer comprising (A) a hydrophobic monomer, (B) a basic monomer and (C) a hydrophilic monomer and (x)=30-95%, (y)=5-70%, (z)=0-60%, all expressed in terms of w/w such that x+y+z=100%, the process comprises dispersion or coating of the drug in a matrix of polymer and lipid component by a technique selected from the group consisting of microencapsulation, spray drying, melt granulation, tray drying method and spray congealing.

In one embodiment of the process, the process comprises microencapsulation using emulsification solvent evaporation method by dissolving the polymer and lipid in an organic solvent selected from chloroform and dichloromethane to form a lipid-polymer solution, and adding the drug to the solution to form an organic phase, dispersing the organic phase in distilled water containing polyvinyl alcohol in an amount of 0.1 to 1% w/w, continuously stirring the mixture mechanically at a rate of about 500-1000 rpm and at a temperature in the range of 25-30° C. for a period in the range of 2-3 hrs and then separating microparticles obtained by filtration and freeze drying the particles for 5-10 hrs.

In another embodiment of the process, the process comprises sizing slabs cast from a solution of the polymer and lipid in dichloromethane or chloroform containing the drug in solution or dispersed form and removal of the solvent by evaporation at 25-30° C.

In another embodiment of the process, the polymer and the drug are dispersed in molten lipid kept at temperature 3-5° C. above the melting point under stirring to obtain a molten mass, which is then gradually cooled to obtain granules, which are then sized.

In another embodiment of the process, the process comprises spray drying the lipid-polymer solution containing the drug to obtain microparticles, which are then dried in the presence of a drying gas selected from the group of nitrogen, argon, carbon dioxide and air.

DETAILED DESCRIPTION OF THE INVENTION

The present invention provides oral pharmaceutical compositions, which effectively inhibit the bitter, unpleasant and otherwise undesirable taste of the active ingredient. More specifically the invention relates to the use of the lipid-polymer blend, which mask the bitter taste of the drugs and also release a substantial amount of drug upon administration without delay at the gastric pH. The composition disclosed in the present application comprises essentially of the acid soluble or swellable polymer in combination with the lipids. The present invention discloses the use of lipid or blend of lipids in combination with the pH dependent polymers such that the pH dependent polymer is acid soluble or swellable. The composition and method of preparation of the polymer is disclosed in our patent co-pending applications PCT/IN03/00390 and PCT/IN03/00392 filed earlier.

Taste masked compositions making use of the synthetic acid soluble polymers and their applications in various pharmaceutical compositions providing substantial immediate release without causing any delay in the absorption of the active ingredient are disclosed in patent applications PCT/IN03/00390 and PCT/IN03/00392. The use of these polymers is effective in taste masking of the drugs to be used in the oral dosage forms like the liquid orals and the solid dosage forms like the chewable, dispersible, rapidly disintegrating tablets. The advantage of these polymers is that they are insoluble at the near neutral pH and are soluble at the acidic pH so that the release of the drug in the stomach is not affected.

Depending on the type of dosage form, the amount of polymer required for imparting palatability will vary. Further the dose of the active ingredient will also affect the performance of the polymer coating. In some cases where the dose is higher, the amount of polymer required to provide effective coating may be more. Liquid dosage forms like dry syrups and suspensions require a more uniform and complete polymer coating to impart taste masking effect and polymer requirement is higher as compared to conventional solid dosage forms.

U.S. patent application Ser. No. 10/971,534 discloses the use of the polymer blends comprising the acid soluble polymer in combination with other pH dependent polymer or pH independent polymers for the taste masking applications. The blend of polymers is used to lower the amount of the each polymer in blend such that it is well within the safe daily allowance as prescribed by the FDA and yet the total amount of the polymer in composition is high enough to provide the taste masking effect. The preferred ratio of total amount of the polymer to drug is 0:5.1 to 4:1 The amount of polymer coating disclosed is essential to prevent the leaching of the drug in the saliva or the aqueous media used to reconstitute the coated granules. Such compositions are of use for the drugs having a wide absorption window along the gastrointestinal tract and also for the immediate release of the drug without delay.

It is desirable to use the minimum amount of polymer to attain the desired drug release rate. The present invention differs from the earlier art in that it further reduces the amount of polymer used for masking unpleasant taste The present invention discloses use of a lipid-polymer matrix for taste masking applications, which reduces the amount of polymer as well as lipid required. The drug to polymer ratio is in the charge of 1:0.1 to 1:1. The compositions of the invention bring about almost immediate and rapid release of the drug. Such compositions with rapid immediate release are of use where the drug is required to be absorbed rapidly to elicit an early therapeutic effect. The compositions also enhance bioavailability of a drug with narrow absorption window restricted to the upper gastric region The acid soluble or swellable polymer used in the composition comprises of monomers methyl methacrylate, hydroxy ethyl methacrylate and vinyl pyridine in the range 50-75%, 15-35% and 5-15% w/w respectively To formulate extremely bitter drugs as dry syrup or suspension, the protective coating has to be sufficiently hydrophobic. Lipids are hydrophobic materials and are hence used extensively in such applications. However because of their hydrophobic nature the release of the drug is delayed. Further the amount of the lipids required to provide the bitterness inhibition is very high. The use of higher loading of the lipids further lowers the rate of release. This affects the bioavailability of the drugs especially in case of the drugs, which have a narrow absorption window, limited to upper gastric region.

The present invention discloses lipid or lipids used in combination with acid soluble or swellable polymer, which dissolves rapidly at gastric pH and facilitates quick dissolution of a drug. Incorporation of the acid soluble/swellable polymer in composition ensures immediate release of drug from the lipid-polymer matrix. The pH dependent polymer of the present invention does not dissolve at pH of saliva and prevents leaching of the drug in the oral cavity Lipids used in the composition of the invention are fatty acids, esters of fatty acid, fatty alcohols, hydrocarbons, neutral fats and waxes. Lipids that are suitable for use in the composition of the invention in general have melting points higher than 40° C. The fatty acids are either saturated or unsaturated. The saturated fatty acids used in the composition are long chain (C10-C24) aliphatic carboxylic acids like lauric acid, stearic acid and palmitic acid. The lipids used comprise fatty alcohol such as stearyl alcohol, palmityl alcohol and cetyl alcohol preferably cetyl alcohol. The esters of fatty acids used comprise esters of glycerol with fatty acids such as glyceryl monostearate, glyceryl monopalmitate, glyceryl tripalmitate, glyceryl behenate and hydrogenated castor oil, preferably glyceryl monostearate and hydrogenated castor oil.

Another feature of the invention is the use of blend of the lipids in combination with the acid soluble or swellable polymer The ratio of pH dependent polymer to lipid in the composition is in the range 1:05 to 1:40 preferably 1:1 to 1:35. The ratio of drug to lipid is in the range 1:0.1 to 1:8, preferably 1:04 to 1:6 The drug and pH dependent polymer ratio is in the range of from 1:0.1 to 1:1 preferably 1:01 to 1:0.6.

The compositions can also be made by microencapsulation of the drug in the lipid-polymer matrix The microencapsulation of the drugs is achieved by emulsification, solvent evaporation or solvent extraction or spray drying of the drug with lipid-polymer solution or dispersion of drug in lipid-polymer solution, preferably microencapsulation by solvent evaporation and spray drying technique. The preferred surfactant is polyvinyl alcohol for microencapsulation by solvent evaporation. Preferably the solvent is selected such that the drug, lipid and the polymer are all soluble in the solvent.

In another feature of the invention the pharmaceutical composition is obtained by dispersing the drug in lipid-polymer matrix either by microencapsulation by solvent evaporation, spray drying, spray congealing, melt granulation or by tray drying method. The solvents chosen for the solubilization of the drug, lipid and polymer are chlorinated hydrocarbons like dichloromethane and chloroform.

The taste-masked microparticles of the drug can be obtained by microencapsulation by emulsification solvent evaporation technique. The dispersed phase is the organic solvent containing the drug dispersed or dissolved in lipid-polymer solution and the dispersion medium is the distilled water. The lipid and polymer is dissolved in the organic solvent The drug is added to this solution and the organic phase is then added into distilled water-containing polyvinyl alcohol (0.1 to 1% w/w). A constant mechanical stirring rate of 500-1000 rpm and at room temperature is maintained for 2-3 hours. The solvent is allowed to evaporate and the microparticles so obtained are separated by filtration and freeze dried for 5-10 hrs.

Alternately particles of the composition can be obtained by spray drying. Lipid and polymer are dissolved in an organic solvent. The drug is either dissolved or dispersed in this solution and spray dried to obtain taste masked micro particles. The drying gas can be an inert gas such as nitrogen, argon and carbon dioxide or air. The preferred gas is air. The gas inlet temperature to the spray dryer depends on the choice of the solvent used but may be in the range of 35-90° C. preferably 35-75° C. The gas outlet temperature is similarly dependent on the solvent but may be in the range of 25-75° C., preferably 25-55° C. The lipid and polymer are solubilized in dichloromethane or chloroform and the drug is either solubilized or dispersed in the lipid-polymer solution. The resulting mixture is spray dried to obtain the micro particles.

The taste masked particles of the present invention can also be obtained by casting of slabs in the tray The lipid and polymer are dissolved in the organic solvent and the drug is either dispersed or solubilized in lipid-polymer solution The resulting solution is poured on the tray to cast the slab. The solvent is allowed to evaporate at 25-30° C. for 2-3 hrs and the residual solvent is removed by drying the slabs at 25-30° C. under vacuum for 24 hrs. The dried material is sized and passed through 40-mesh sieve.

Lipids do not form good films hence integral coatings with lipids alone need larger amount of lipids to disperse the medicament completely in the lipid matrix. The techniques like the melt granulation and spray congealing also need large amount of the molten lipids since the drug is required to be dispersed within the lipid matrix. The large amount of the lipid required to disperse the drug during melt granulation is evident from the amount of the lipid required in example 5 and example 9, in comparison to the amount of lipid used in other examples disclosed herein. Another feature of the present invention is to use the lipid polymer solution in a solvent to disperse the drug in the lipid polymer matrix such that the amount of the lipid required in the compositions is reduced.

The taste masked particles of the invention can also be obtained by melt granulation. The lipid is placed in the jacketed vessel attached to circulating water bath. The temperature of the circulating water is set, such that the lipid is maintained at 3-5° C. above the melting point. The polymer is dispersed in the molten lipid under stirring followed by the addition of the drug. The temperature of circulating water is gradually lowered to cool the molten lipid. The solid mass thus obtained is sized and passed thorough 40-mesh sieve.

The drug release from the compositions containing higher loadings of lipids as exemplified in example 5 and 9 is slower in comparison to the other compositions employing lower amounts of lipids in combination with the polymer.

The taste masked particles and granules obtained in the present invention may be mixed with flavoring agents such as natural or artificial flavors, citric and tartaric acids, sweeteners such as sucrose, saccharin and aspartame, and other pharmaceutically acceptable excipients to be formulated as conventional, chewable or dispersible tablets, dry syrups, suspensions, sachets or any other suitable oral dosage form. The taste masked particles and granules obtained in the present invention may comprise of the blend of acid soluble or swellable polymer and lipid and can be suspended using the reconstitution medium of pH >3.5.

This disclosure also compares release of a drug from a dry syrup product containing cefuroxime axetil particles having integral stearic acid coating (commercially available as Ceftum manufactured by Glaxo Wellcome Operations, Harmire Road, Barnard Castle County Durham, DL 12 8DT, UK, Marketed by Glaxo India Limited) with compositions of the present invention Cefuroxime axetil is better absorbed from upper gastric region as compared to intestinal region Dantzig et al (Anne H. Dantzig, Dale C. Duckworth, Linda B. Tabas, Biochimica et Biophysica Acta 1191, 1994, 7-13) show that cefuroxime axetil is hydrolyzed to cefuroxime in intestinal lumen by esterases, reducing cefuroxime axetil concentration in lumen resulting in reduced absorption, leading to low bioavailability of Cefuroxime axetil in humans Cefuroxime axetil already has low bioavailability of 32-50%. Thus further reduction in bioavailability due to formulation aspects should be minimized. Dissolution of the market product was therefore carried out in acidic pH using 0.07 N HCl as medium, which is a dissolution medium for cefuroxime axetil tablets (monograph in US Pharmacopoeia 26).

The dissolution of the Ceftum sample containing cefuroxime axetil was done on sample weight 4.18 g equivalent to one dose of 125 mg (41.8 g/50 ml with 5 ml equivalent to 125 mg of cefuroxime). The sample was wetted in dissolution media removed from 900 ml of media prior to dissolution and then placed in dissolution vessel again. The glass beaker used for weaving the sample was rinsed with dissolution media removed in excess prior to dissolution and again placed in the dissolution vessel. Cefuroxime axetil release was determined in buffer media comprising 900 ml of 0.07 N hydrochloric acid, using USP type II apparatus rotated at 100 rpm at 37±0.5° C. Samples were withdrawn at 30, 60, 120, 180 and 240 min. The amount withdrawn each time was replaced with fresh media to maintain the sink conditions. The amount of drug released is 40% in 30 min, 50% in 60 min, 64.6% in 120 min, 69.5% in 180 min and 77.17% in 240 min.

Examples 1 and 2 disclose a method of preparing acid soluble/swellable polymer. The taste masked pharmaceutical compositions as exemplified in the examples 3 to 9, given below were tested for drug release with respect to time. The sample was wetted in the dissolution media removed from 900 ml of media prior to the dissolution and then placed in dissolution vessel again. The glass beaker used for wetting the sample was rinsed with the dissolution media removed in excess prior to dissolution and again placed in the dissolution vessel.

Cefuroxime axetil release from the taste masked particles was determined in 900 ml of 0.07 N hydrochloric acid maintained at 37±0.5° C., using USP type II apparatus rotated at 100 rpm. The samples were withdrawn at 30, 60, 120, 180 and 240 min. The amount withdrawn each time was replaced with fresh media to maintain the sink conditions.

Ciprofloxacin hydrochloride release from the taste masked particles was determined in 900 ml of 0.01 N hydrochloric acid buffer, at 37±0.5° C., using USP type II apparatus rotated at 100 rpm Samples were withdrawn at 30, 60, 120, 180 and 240 min. The amount withdrawn each time was replaced with fresh media to maintain sink conditions. The pharmaceutical compositions of the invention mask the bitter taste of drugs and do not release the drug at pH of saliva but release the drug with no delay at pH of stomach and are not soluble in water.

The taste making compositions and the properties thereof are described herein below with reference to the following illustrative and non-limiting examples.

EXAMPLE 1

Acid soluble or swellable polymer was synthesized by solution polymerization. A hydrophobic monomer, basic monomer and optionally a hydrophilic monomer were dissolved dimethyl formamide solvent The polymer has a monomer composition Methyl methacrylate 65% by wt Hydroxyethyl methacrylate 24% by wt and Vinyl Pyridine 11% by wt. An azo initiator, azo bis isobutyronitrile was added to the monomer solution in dimethyl formamide. Reaction mixture was purged with nitrogen gas to provide inert atmosphere. Polymerization reaction was carried out by heating the reaction mixture to 65° C. for a period of 18 hours. The polymer so synthesized was recovered by precipitation, in a nonsolvent (here water), and was dried at 45°

C. under vacuum. Molecular weight of polymer synthesized was determined using Waters gel permeation chromatography and polystyrene standard (Polysciences Inc USA) as reference using Styragel columns. The molecular weight of the polymer is 53,000.

EXAMPLE 2

Acid soluble or swellable polymer was synthesized by solution polymerization. A hydrophobic monomer, basic monomer and optionally a hydrophilic monomer were dissolved dimethyl formamide solvent. The polymer has a monomer composition Methyl methacrylate 73% by wt Hydroxyethyl methacrylate 18% by wt and Vinyl Pyridine 9% by wt. Azo initiator, azo bis isobutyronitrile was added to monomer solution in dimethyl formamide. Reaction mixture was purged with nitrogen gas to provide inert atmosphere. The polymerization reaction was carried out by heating reaction mixture to 65° C. for a period of 18 hours. The polymer so synthesized was recovered by precipitation in a nonsolvent (here water) and dried at 45° C. under vacuum. Molecular weight of polymer synthesized was determined using Waters gel permeation chromatography and polystyrene standard (Polysciences Inc. USA) as reference using Styragel columns The molecular weight of the polymer is 52,000.

EXAMPLE 3

The taste masked compositions are made by dissolving the drug in a solution of lipid and polymer in organic solvent and obtaining the microparticles containing the drug by microencapsulation in water and evaporation of the organic solvent.

Lipid-Polymer solution: Compositions containing various lipid-polymer blends are shown in Table 1 The acid soluble polymer prepared in example 1 is used in all compositions as one of the pH dependent polymers. Amount of solvent used is 7 ml of chlorinated hydrocarbons like chloroform and dichloromethane Amount of lipid and polymer are shown in table 1

The taste masked microparticles were obtained by emulsification solvent evaporation technique. Cefuroxime axetil was dissolved in lipid-polymer solution made with requisite amount of solvent The lipid-polymer solution containing the drug was added dropwise to distilled water bath under mechanical stirring. Polyvinyl alcohol was added to the distilled water 0.1% by weight, to facilitate the dispersion of the lipid-polymer solution containing the drug. A constant mechanical stirring rate of 500 rpm and at room temperature was maintained for a 3-4 hours. The solvent was allowed to evaporate and the microparticles so obtained were separated by filtration, and freeze dried for 7 hrs. The drug release pattern of the composition prepared was monitored and the results are tabulated in Table 2

TABLE 1

| S. No. | Lipid | pH dependent polymer | Drug |
| --- | --- | --- | --- |
| 1 | Stearic acid 0.45 g | Acid Soluble polymer 0.15 g | Cefuroxime axetil 0.3 g |
| 2 | Palmitic acid 0.50 g | Acid Soluble polymer 0.3 g | Cefuroxime axetil 0.6 g |
| 3 | Cetyl Alcohol 0.40 g | Acid Soluble polymer 0.2 g | Cefuroxime axetil 0.6 g |

TABLE 2

| S. No | Composition | % Drug released in 30 min |
| --- | --- | --- |
| 1 | Stearic acid 0.45 g Acid Soluble polymer 0.15 g Cefuroxime axetil 0.3 g | 98.0 |
| 2 | Palmitic acid 0.50 g Acid Soluble polymer 0.3 g Cefuroxime axetil 0.6 g | 99.6 |
| 3 | Cetyl Alcohol 0.4 g Acid Soluble polymer 0.2 g Cefuroxime axetil 0.6 g | 96.8 |

EXAMPLE 4

Taste masked compositions are made by casting slabs of lipid-polymer containing the drug. The lipid-polymer solution in organic solvent is cast in a tray containing the drug in a solution form or in a dispersed form. Solvent is allowed to evaporate and particles are obtained by sizing the mass through 40-mesh sieve.

Lipid-Polymer solution Compositions containing various lipid-polymer blends are shown in Table 3 Acid soluble polymer prepared in example 1 is used in all coating compositions as one of the pH dependent polymers. Amount of solvent used is 7 ml of chlorinated hydrocarbons like chloroform and dichloromethane. Amount of lipid and polymer are also shown in Table 3

Taste masked particles are prepared by sizing the mass obtained by casting of lipid-polymer slab containing drug in dispersed form Ciprofloxacin hydrochloride was added to lipid-polymer solution in chloroform made with requisite amount of solvent Lipid-polymer solution containing the drug was poured in a tray to cast the slab. Solvent was allowed to evaporate at 25° C. for 2-3 hrs Residual solvent was removed by placing the composition in vacuum at 25° C. for 24 hrs. Drug release pattern of the composition prepared was monitored and results are tabulated in Table 4.

TABLE 3

| S. No | Lipid | pH dependent polymer | Drug |
| --- | --- | --- | --- |
| 1 | Stearic acid 0.844 g | Acid Soluble Polymer 0.10 g | Ciprofloxacin HCL 0.583 g |
| 2 | Palmitic acid 0.844 g | Acid Soluble Polymer 0.10 g | Ciprofloxacin HCL 0.583 g |
| 3 | Cetyl Alcohol 0.844 g | Acid Soluble Polymer 0.10 g | Ciprofloxacin HCL 0.583 g |
| 4 | Palmitic Acid 0.422 g Stearic Acid 0.422 g | Acid Soluble Polymer 0.10 g | Ciprofloxacin HCL 0.583 g |
| 5 | Stearic acid 0.422 g Cetyl Alcohol 0.422 g | Acid Soluble Polymer 0.10 g | Ciprofloxacin HCL 0.583 g |

TABLE 4

| | | % Drug released (min) | | | |
| --- | --- | --- | --- | --- | --- |
| S. No | Composition | 30 | 60 | 120 | 180 |
| 1 | Stearic acid 0.844 g Acid Soluble polymer 0.1 g Ciprofloxacin HCL 0.583 g | 83.8 | 87.7 | 88.0 | 93.3 |
| 2 | Palmitic acid 0.844 g Acid Soluble polymer 0.10 g Ciprofloxacin HCL 0.583 g | 91.5 | 95.0 | 96.2 | 98.0 |
| 3 | Cetyl Alcohol 0.844 g Acid Soluble polymer 0.1 g | 91.1 | 92.4 | 94.2 | 95.0 |

TABLE 4-continued

| S. No | Composition | % Drug released (min) | | | |
|---|---|---|---|---|---|
| | | 30 | 60 | 120 | 180 |
| 4 | Ciprofloxacin HCL 0.583 g<br>Palmitic acid 0.422 g<br>Stearic Acid 0.422 g<br>Acid Soluble polymer 0.1 g<br>Ciprofloxacin HCL 0.583 g | 88.8 | 90.8 | 92.0 | 93.0 |
| 5 | Cetyl Alcohol 0.422 g<br>Stearic Acid 0.422 mg<br>Acid Soluble polymer 0.1 g<br>Ciprofloxacin HCL 0.583 g | 82.5 | 90.0 | 94.3 | 97.3 |

EXAMPLE 5

Taste masked particles are obtained by melt granulation method. Lipid is placed in a jacketed vessel attached to a circulating water bath. Temperature of circulating water is set such that lipid is maintained at 3-5° C. above melting point thereof Acid soluble polymer prepared in example 2 is used in the compositions The polymer is dispersed in molten lipid under stirring followed by addition of Ciprofloxacin Hydrochloride. Temperature of circulating water is gradually lowered to cool the molten lipid. The solid mass thus obtained is sized by passing thorough 40-mesh sieve. The compositions containing various lipid-polymer blends are shown in Table 5 Drug release pattern of the composition prepared was monitored and results are tabulated in Table 6

TABLE 5

| S. No | Lipid | pH dependent polymer | Drug |
|---|---|---|---|
| 1 | Stearic acid 1.75 g | Acid Soluble Polymer 0.10 g | Ciprofloxacin HCL 0.583 g |
| 2 | Palmitic Acid 0.873 g<br>Stearic Acid 0.873 g | Acid Soluble Polymer 0.10 g | Ciprofloxacin HCL 0.583 g |

TABLE 6

| S. No | Composition | % Drug released (min) | | | | |
|---|---|---|---|---|---|---|
| | | 30 | 60 | 120 | 180 | 240 |
| 1 | Stearic acid 1.75 g<br>Acid Soluble polymer 0.1 g<br>Ciprofloxacin HCL 0.583 g | 69.8 | 77.5 | 84.5 | 87.0 | 94.7 |
| 2 | Palmitic acid 0.873 g<br>Stearic Acid 0.873 g<br>Acid Soluble polymer 0.1 g<br>Ciprofloxacin HCL 0.583 g | 70.5 | 75.4 | 80.0 | 84.0 | 92.0 |

EXAMPLE 6

The taste masked microparticles are obtained by spray drying. The lipid and polymer are dissolved in an organic solvent, the drug is either dissolved or dispersed in this solution and spray dried to obtain the taste masked microparticles The drying gas can be an inert gas such as nitrogen, argon and carbon dioxide or air The preferred gas in the present invention is air. The gas inlet temperature to the spray is in the range 35-75° C. The gas outlet temperature is in the range of 35-55° C. Lipid and polymer are solubilized in chloroform and cefuroxime axetil is solubilized in the lipid-polymer solution The acid soluble polymer prepared in example 1 is used in composition. The resulting mixture is spray dried to obtain the micro particles. The compositions containing various lipid-polymer blends are shown in the table 7. Drug release pattern of the compositions prepared was monitored and results are tabulated in Table 8.

TABLE 7

| S. No | Lipid | pH dependent polymer | Drug |
|---|---|---|---|
| 1 | Stearic acid 3.0 g | Acid Soluble Polymer 1.0 g | Cefuroxime axetil 3.0 gm |
| 2 | Stearic acid 1.5 g<br>Plamitic acid 1.5 g | Acid Soluble Polymer 1.0 g | Cefuroxime axetil 3.0 gm |
| 3 | Stearic acid 2.0 g<br>Glyceryl monostearate 1.0 g | Acid Soluble Polymer 1.0 g | Cefuroxime axetil 3.0 gm |
| 4 | Stearic acid 2.0 g<br>Hydrogenated Castor Oil 1.0 g | Acid Soluble Polymer 1.0 g | Cefuroxime axetil 3.0 gm |

TABLE 8

| S. No | Composition | % Drug released (min) | | | |
|---|---|---|---|---|---|
| | | 30 | 60 | 120 | 180 |
| 1 | Stearic acid 3.0 g<br>Acid Soluble polymer 0.1 g<br>Cefuroxime Axetil 3.0 g | 70.7 | 81.0 | 92.6 | 93.2 |
| 2 | Palmitic acid 1.5 g<br>Stearic Acid 1.5 g<br>Acid Soluble polymer 1.0 g<br>Cefuroxime axetil 3.0 g | 87.4 | 95.1 | 98.4 | — |
| 3 | Stearic acid 2.0 g<br>Glyceryl monostearate 1.0 g<br>Acid Soluble Polymer 1.0 g<br>Cefuroxime axetil 3.0 gm | 96.5 | 97.5 | 98.0 | — |
| 4 | Stearic acid 2.0 g<br>Hydrogenated Castor oil 1.0 g<br>Acid Soluble Polymer 1.0 g<br>Cefuroxime axetil 3.0 gm | 73.3 | 81.2 | 91.4 | 97.0 |

EXAMPLE 9

The taste masked particles are obtained by the melt granulation method. The lipid is placed in the jacketed vessel attached to circulating water bath. The temperature of the circulating water is set such that the lipid is maintained at 3-5° C. above the melting point of the lipid. The acid soluble polymer prepared in example 2 is used in the compositions. The polymer is dispersed in the molten lipid under stirring followed by addition of Cefuroxime axetil. The temperature of the circulating water is gradually lowered to cool the molten lipid The solid mass thus obtained is sized by passing thorough 40-mesh sieve. The compositions containing the various lipid-polymer blends are shown in the table 9 The drug release pattern of the composition prepared was monitored and the results are tabulated in Table 10

TABLE 9

| S. No | Lipid | pH dependent polymer | Drug |
|---|---|---|---|
| 1 | Stearic acid 3.6 g | Acid Soluble Polymer 0.150 g | Cefuroxime axetil 0.9 g |
| 2 | Cetyl Alcohol 2.3 g | Acid Soluble Polymer 0.150 g | Cefuroxime axetil 0.90 gm |
| 3 | Palmitic Acid 1.2 g<br>Stearic Acid 1.2 g | Acid Soluble Polymer 0.200 g | Cefuroxime axetil 0.450 g |

TABLE 9-continued

| S. No | Lipid | pH dependent polymer | Drug |
|---|---|---|---|
| 4 | Lauric Acid 2.4 g | Acid Soluble Polymer 0.2 g | Cefuroxime axetil 0.45 g |
| 5 | Palmitic Acid 2.4 g | Acid Soluble Polymer 0.2 g | Cefuroxime axetil 0.450 g |

TABLE 10

| | | % Drug released Time in min | | | | |
|---|---|---|---|---|---|---|
| S No | Composition | 30 | 60 | 120 | 180 | 240 |
| 1 | Stearic acid 3.6 g<br>Acid Soluble polymer 0.15 g<br>Cefuroxime Axetil 0.9 g | 55.4 | 61.0 | 65.0 | 71.0 | 73.0 |
| 2 | Cetyl Alcohol 2.3 g<br>Acid Soluble polymer 0.15 g<br>Cefuroxime axetil 0.9 g | 54.7 | 64.6 | 70.0 | 78.0 | 81.5 |
| 3 | Palmitic Acid 1.2 g<br>Stearic Acid 1.2 g<br>Acid Soluble Polymer 0.200 g<br>Cefuroxime axetil 0.450 g | 53.6 | 58.7 | 62.0 | 68.0 | 72.0 |
| 4 | Lauric Acid 2.4 g<br>Acid Soluble Polymer 0.2 g<br>Cefuroxime axetil 0.45 g | 62.4 | 64.5 | 70.0 | 77.13 | 82.2 |
| 5 | Palmitic Acid 2.4 g<br>Acid Soluble Polymer 0.2 g<br>Cefuroxime axetil 0.450 g | 55.3 | 62.0 | 65.0 | 73.3 | 78.0 |

The Advantages of the Present Invention are as Follows:

1. The compositions described herein comprise reverse enteric or acid soluble polymer in combination with the lipid or blend of lipids, which facilitates the rapid release of the drug in the gastric pH and the total amount of the polymer required with respect to the drug in the compositions is lowered.
2. The fatty acids are known for the taste masking applications however for complete coating of drug large amounts are required and since they are hydrophobic, the drug release is delayed. The present invention discloses the use of the pH dependent polymer, which remains collapsed at the pH of saliva and hence acts synergistically for the taste inhibition. However the polymer solubilizes at the gastric pH and releases substantial amount of the drug without any delay.
3. The present invention discloses the use of the acid soluble polymer along with the lipids wherein the polymer remains collapsed in water and also in pH >3.5. These preparations have the advantage over the compositions using the blends of water soluble polymers and lipids the later formulations are not suitable for the liquid oral preparations.
4. The use of the acid soluble polymer together with the fatty acid helps in achieving the taste masking at lower loading of the fatty acids and the polymer. The use of lipid polymer solution to disperse the drug in the lipid-polymer matrix further lowers the amount of lipid required in the compositions to taste mask the bitter drug.
5. The use of acid soluble polymer in compositions aids in releasing the drug in the acidic pH of the stomach without delay and further the polymer does not release the drug at pH of saliva. Such compositions would therefore provide immediate and also near complete release of the drug unlike the compositions using the lipids in combination with the pH independent polymers and enteric polymers.
6. The acid soluble polymer used in the present inventions does not exhibit any negative interaction with the drug cefuroxime axetil as is exhibited by the reverse enteric coating materials comprising dimethyl aminoethyl methacrylate like Eudragit E. Thus the compositions of present invention comprising the lipid-polymer matrix are suitable for the drugs, which exhibit negative interactions with Eudragit E.
7. The use of the acid soluble polymers, which remain collapsed above the pH 3.5, is that they provide a greater flexibility for the taste masking compositions like dry syrup or suspension compositions which are required to be reconstituted at pH 3.5 and above unlike the systems incorporating the reverse enteric polymer Eudragit E, since Eudragit E exhibits swelling up to pH 5.5.
8. The compositions using the acid soluble polymer in the present compositions release the drug rapidly in comparison to the amount released from the marketed composition Ceftum based on the integral lipid coating of the drug by stearic acid alone. This is advantageous in case of the bitter drug cefuroxime axetil as it is better absorbed from the upper gastric region.

We claim:

1. A pharmaceutical composition comprising a drug, a lipid component and a pH dependent polymer wherein the pH dependent polymer is acid soluble or swellable and has a formula: P $[A_{(x)}B_{(y)}C_{(z)}]$ wherein P is polymer comprising (A) a hydrophobic monomer, (B) a basic monomer and (C) a hydrophilic monomer and (x)=30-95%, (y)=5-70%, (z)=0-60%, all expressed in terms of w/w such that, x+y+z=100%, and the drug is dispersed or coated in a matrix of the polymer and lipid component.

2. A composition as claimed in claim 1 wherein the pH dependent polymer is selected from the group consisting of an acid soluble polymer or an acid swellable polymer.

3. A composition as claimed in claim 1 wherein the acid soluble or swellable polymer consists of monomers methyl methacrylate, hydroxy ethyl methacrylate and vinyl pyridine in the range of 50-75%, 15-35% and about 5-15% w/w respectively.

4. A composition as claimed in claim 1 wherein the lipid component is selected from the group consisting of fatty acids, esters of fatty acid, fatty alcohols, hydrocarbons, neutral fats and waxes.

5. A composition as claimed in claim 4 wherein the fatty acid is selected from the group of saturated or unsaturated fatty acid.

6. A composition as claimed in claim 5 wherein the saturated fatty acid comprises a long chain aliphatic carboxylic acid selected from the group consisting of lauric acid, stearic acid and palmitic acid.

7. A composition as claimed in claim 4 wherein the fatty alcohol comprises a long chain aliphatic alcohol selected from the group consisting of stearyl alcohol, palmityl alcohol and cetyl alcohol.

8. A composition as claimed in claim 4 wherein the fatty alcohol is cetyl alcohol.

9. A composition as claimed in claim 4 wherein the ester of fatty acid comprises an ester of glycerol with a fatty acid and is selected from the group consisting of glyceryl monostearate, glyceryl monopalmitate, glyceryl tripalmitate, glyceryl behenate and hydrogenated castor oil.

10. A composition as claimed in claim 4 wherein the ester of fatty acid is selected from glyceryl monostearate and hydrogenated castor oil.

11. A composition as claimed in claim 1 wherein the lipid component is used as a single lipid or a combination of lipids.

12. A composition as claimed in claim 1 wherein the ratio of pH dependent polymer to lipid component is in the range of 1:0.5 to 1:40.

13. A composition as claimed in claim 1 wherein the ratio of pH dependent polymer to lipid component is in the range of 1:1 to 1:35.

14. A composition as claimed in claim 1 wherein the ratio of drug to lipid is in the range of 1:0.1 to 1:8.

15. A composition as claimed in claim 1 wherein the ratio of drug to lipid is in the range of 1:04 to 1:06.

16. A composition as claimed in claim 1 wherein the ratio of drug to pH dependent polymer is in the range of 1:0.1 to 1:1.

17. A composition as claimed in claim 1 wherein the ratio of drug to pH dependent polymer is in the range of 1:0.1 to 1:0.6.

18. A composition as claimed in claim 1 wherein the drug is used as such or in the form of a pharmaceutically acceptable salt or ester or amide thereof.

19. A composition as claimed in claim 1 wherein the drug is selected from the group consisting of macrolide antibiotics selected in turn from the group consisting of erythromycin, azithromycin and clarithromycin; fluroquinolones selected in turn from the group consisting of ciprofloxacin, enrofloxacin, ofloxacin, gatifloxacin, levofloxacin and norfloxacin; cephalosporins selected in turn from the group consisting of cefuroxime, cefaclor, cephalexin, cephadroxil and cepfodoxime proxetil; nonsteoroidal, anti-inflammatory and analgesic drugs selected in turn from the group consisting of ibuprofen, aspirin, acetaminophen and diclofenac sodium, COX 2 inhibitors selected in turn from the group consisting of etaricoxib and celecoxib; antihistamic drugs selected in turn from the group consisting of cimetidine, ranitidine, famotidine and chlorpheniramine maleate; oxazolidinones comprising linezolid; and dextromethorphan.

20. A composition as claimed in claim 1 wherein the composition is in the form of particles, with the drug dispersed within a polymer-lipid matrix.

21. A composition as claimed in claim 1 wherein the composition comprises particles by themselves or in a pharmaceutically acceptable dosage form.

22. A composition as claimed in claim 1 wherein the composition is in the form of liquid orals selected from dry syrups and suspensions.

23. A composition as claimed in claim 1 wherein the composition is in the form of solid dosage forms selected from the group consisting of chewable tablets, effervescent tablets, rapidly disintegrating tablets and dispersible tablets.

24. A process for the preparation of a pharmaceutical composition comprising a drug, a lipid component and a pH dependent polymer wherein the pH dependent polymer is acid soluble or swellable and has a formula: P $[A_{(x)}B_{(y)}C_{(z)}]$ wherein P is polymer comprising (A) a hydrophobic monomer, (B) a basic monomer and (C) a hydrophilic monomer and (x)=30-95%, (y)=5-70%, (z)=0-60%, all expressed in terms of w/w such that, x+y+z=100%, wherein the process comprises dispersion or coating of the drug in a matrix of the polymer and lipid component by a technique selected from the group consisting of microencapsulation, spray drying, melt granulation, tray drying method and spray concealing.

25. A process as claimed in claim 24 wherein the process comprises microencapsulation using emulsification solvent evaporation method by dissolving the polymer and lipid in an organic solvent selected from chloroform and dichloromethane to form a lipid-polymer solution, and adding the drug to the solution to form an organic phase, dispersing the organic phase in distilled water containing polyvinyl alcohol in an amount of 0.1 to 1% w/w, continuously stirring the mixture mechanically at a rate of about 500-1000 rpm and at a temperature in the range of 25-30° C. for a period in the range of 2-3 hrs and then separating microparticles obtained by filtration and freeze drying the particles for 5-10 hrs.

26. A process as claimed in claim 24 wherein the process comprises sizing slabs cast from a solution of the polymer and lipid in dichloromethane or chloroform containing the drug in solution or dispersed form and removal of the solvent by evaporation at 25-30° C.

27. A process as claimed in claim 24 wherein the polymer and the drug are dispersed in molten lipid kept at temperature 3-5° C. above the melting point under stirring to obtain a molten mass, which is then gradually cooled to obtain granules, which are then sized.

28. A process as claimed in claim 24 wherein the process comprises spray drying the lipid-polymer solution containing the drug to obtain microparticles, which are then dried in the presence of a drying gas selected from the group of nitrogen, argon, carbon dioxide and air.

29. A process as claimed in claim 28 wherein the drying gas is air.

30. A process as claimed in claim 24 wherein the pH dependent polymer is selected from the group consisting of an acid soluble polymer or an acid swellable polymer.

31. A process as claimed in claim 24 wherein the acid soluble or swellable polymer consists of monomers methyl methacrylate, hydroxy ethyl methacrylate and vinyl pyridine in the range of 50-75%, 15-35% and about 5-15% w/w respectively.

32. A process as carried in claim 24 wherein the lipid component is selected from the group consisting of fatty acids, esters of fatty acid, fatty alcohols, hydrocarbons, neutral fats and waxes.

33. A process as claimed in claim 32 wherein the fatty acid is selected from the group of saturated or unsaturated fatty acid.

34. A process as claimed in claim 33 wherein the saturated fatty acid comprises a long chain aliphatic carboxylic acid selected from the group consisting of lauric acid, stearic acid and palmitic acid.

35. A process as claimed in claim 32 wherein the fatty alcohol comprises a long chain aliphatic alcohol selected from the group consisting of stearyl alcohol, palmityl alcohol and cetyl alcohol.

36. A process as claimed in claim 32 wherein the fatty alcohol is cetyl alcohol.

37. A process as claimed in claim 32 wherein the ester of fatty acid comprises an ester of glycerol with a fatty acid and is selected from the group consisting of glyceryl monostearate, glyceryl monopalmitate, glyceryl tripalmitate, glyceryl behenate and hydrogenated castor oil.

38. A process as claimed in claim 32 wherein the ester of fatty acid is selected from glyceryl monostearate and hydrogenated castor oil.

39. A process as claimed in claim 24 wherein the lipid component is used as a single lipid or a combination of lipids.

40. A process as claimed in claim 24 wherein the ratio of pH dependent polymer to lipid component is in the range of 1:0.5 to 1:40.

41. A process as claimed in claim 24 wherein the ratio of pH dependent polymer to lipid component is in the range of 1:1 to 1:35.

42. A process as claimed in claim 24 wherein the ratio of drug to lipid is in the range of 1:0.1 to 1:8.

43. A process as claimed in claim 24 wherein the ratio of drug to lipid is in the range of 1:0.4 to 1:6.

44. A process as claimed in claim 24 wherein the ratio of drug to pH dependent polymer is in the range of 1:0 to 1:1.

45. A process as claimed in claim 24 wherein the ratio of drug to pH dependent polymer is in the range of 1:0.1 to 1:0.6.

46. A process as claimed in claim 24 wherein the drug is used as such or in the form of a pharmaceutically acceptable salt or ester or amide thereof.

47. A process as claimed in claim 24 wherein the drug is selected from the group consisting of macrolide antibiotics selected in turn from the group consisting of erythromycin, azithromycin and clarithromycin, fluroquinolones selected in turn from the group consisting of ciprofloxacin, enrofloxacin, ofloxacin, gatifloxacin, levofloxacin and norfloxacin cephalosporins selected in turn from the group consisting of cefuroxime, cefaclor, cephalexin, cephadroxil and cepfodoxime proxetil; nonsteoroidal; anti-inflammatory and analgesic drugs selected in turn from the group consisting of ibuprofen, aspirin, acetaminophen and diclofenac sodium; COX 2 inhibitors selected in turn from the group consisting of etoricoxib and celecoxib, antihistamic drugs selected in turn from the group consisting of cimetidine, ranitidine, famotidine and chlorpheniramine maleate; oxazolidinones comprising linezolid; and dextromethorphan.

48. A process as claimed in claim 24 wherein the composition is in the form of particles, with the drug dispersed within a polymer-lipid matrix.

49. A process as claimed in claim 24 wherein the composition comprises particles by themselves or in a pharmaceutically acceptable dosage form.

50. A process as claimed in claim 24 wherein the composition is in the form of liquid orals selected from dry syrups and suspensions.

51. A process as claimed in claim 24 wherein the composition is in the form of solid dosage forms selected from the group consisting of chewable tablets, effervescent tablets, rapidly disintegrating tablets and dispersible tablets.

* * * * *